(12) United States Patent
Duncan et al.

(10) Patent No.: US 9,771,085 B2
(45) Date of Patent: *Sep. 26, 2017

(54) ROBOTIC VEHICLE CONTROL

(71) Applicant: Elwha LLC, Bellevue, WA (US)

(72) Inventors: William D. Duncan, Mill Creek, WA (US); Roderick A. Hyde, Redmond, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/157,130

(22) Filed: May 17, 2016

(65) Prior Publication Data

US 2016/0257311 A1    Sep. 8, 2016

Related U.S. Application Data

(63) Continuation of application No. 14/091,060, filed on Nov. 26, 2013, now Pat. No. 9,364,178.

(51) Int. Cl.
| | | |
|---|---|---|
| *G05D 1/00* | (2006.01) | |
| *B60W 50/08* | (2012.01) | |
| *A61B 5/18* | (2006.01) | |
| *B60W 30/00* | (2006.01) | |
| *A61B 5/00* | (2006.01) | |

(52) U.S. Cl.
CPC ............. *B60W 50/082* (2013.01); *A61B 5/18* (2013.01); *A61B 5/6893* (2013.01); *B60W 30/00* (2013.01); *G05D 1/0061* (2013.01); *G05D 1/0088* (2013.01); *A61B 2560/0242* (2013.01); *G05D 2201/0213* (2013.01)

(58) Field of Classification Search
CPC .............................. B60W 30/00; B60W 40/08
USPC .......................................................... 701/29.2
See application file for complete search history.

(56) References Cited

U.S. PATENT DOCUMENTS

| | | |
|---|---|---|
| 6,474,683 B1 | 11/2002 | Breed et al. |
| 6,793,242 B2 | 9/2004 | Breed et al. |
| 6,950,022 B2 | 9/2005 | Breed |
| 7,082,359 B2 | 7/2006 | Breed |
| 7,639,148 B2 | 12/2009 | Victor |
| 7,834,867 B2 | 11/2010 | Sprague et al. |

(Continued)

FOREIGN PATENT DOCUMENTS

| | | |
|---|---|---|
| JP | 2009-269431 | 11/2009 |
| KR | 2008/0010151 | 1/2008 |

OTHER PUBLICATIONS

International Search Report for Application No. PCT/US2014/067119, Mar. 27, 2015; pp. 1-4.

*Primary Examiner* — Redhwan K Mawari
*Assistant Examiner* — Anshul Sood
(74) *Attorney, Agent, or Firm* — Foley & Lardner LLP

(57) ABSTRACT

A vehicle includes a detection system configured to acquire data regarding operation of the vehicle, and a robotic driving device configured to provide robotic control of the vehicle. The vehicle also includes a control system configured to determine whether the robotic driving device is activated, such that the vehicle is in robotic driving mode; receive a request by a prospective operator of the vehicle to deactivate the robotic driving device to initiate a manual driving mode; determine whether the prospective operator is impaired based on the data; and selectively grant or refuse the request based on the determination.

22 Claims, 8 Drawing Sheets

(56) References Cited

U.S. PATENT DOCUMENTS

| | | |
|---|---|---|
| 7,894,951 B2 | 2/2011 | Norris et al. |
| 7,956,858 B2 | 6/2011 | Sprague et al. |
| 7,978,189 B2 | 7/2011 | Sprague et al. |
| 7,986,315 B2 | 7/2011 | Sprague et al. |
| 8,126,642 B2 | 2/2012 | Trepagnier et al. |
| 8,280,623 B2 | 10/2012 | Trepagnier et al. |
| 8,355,013 B2 | 1/2013 | Sprague et al. |
| 2003/0002690 A1 | 1/2003 | Breed et al. |
| 2003/0136600 A1 | 7/2003 | Breed et al. |
| 2005/0125117 A1 | 6/2005 | Breed |
| 2006/0220883 A1 | 10/2006 | Matos |
| 2007/0219720 A1 | 9/2007 | Trepagnier et al. |
| 2007/0273794 A1 | 11/2007 | Sprague et al. |
| 2008/0122636 A1 | 5/2008 | Matos |
| 2010/0106356 A1 | 4/2010 | Trepagnier et al. |
| 2010/0305778 A1 | 12/2010 | Dorneich et al. |
| 2011/0018986 A1 | 1/2011 | Sprague et al. |
| 2011/0025930 A1 | 2/2011 | Sprague et al. |
| 2011/0025983 A1 | 2/2011 | Sprague et al. |
| 2011/0210867 A1 | 9/2011 | Benedikt |
| 2011/0234919 A1 | 9/2011 | Sprague et al. |
| 2011/0282130 A1 | 11/2011 | Krueger |
| 2012/0101680 A1 | 4/2012 | Trepagnier et al. |
| 2012/0112879 A1* | 5/2012 | Ekchian .................. A61B 5/117 340/5.53 |
| 2012/0206252 A1 | 8/2012 | Sherony et al. |
| 2012/0283912 A1 | 11/2012 | Lee et al. |
| 2013/0070043 A1 | 3/2013 | Geva et al. |
| 2013/0131907 A1 | 5/2013 | Green et al. |
| 2013/0304514 A1 | 11/2013 | Hyde et al. |
| 2014/0375462 A1 | 12/2014 | Biondo et al. |
| 2015/0066284 A1 | 3/2015 | Yopp |

\* cited by examiner

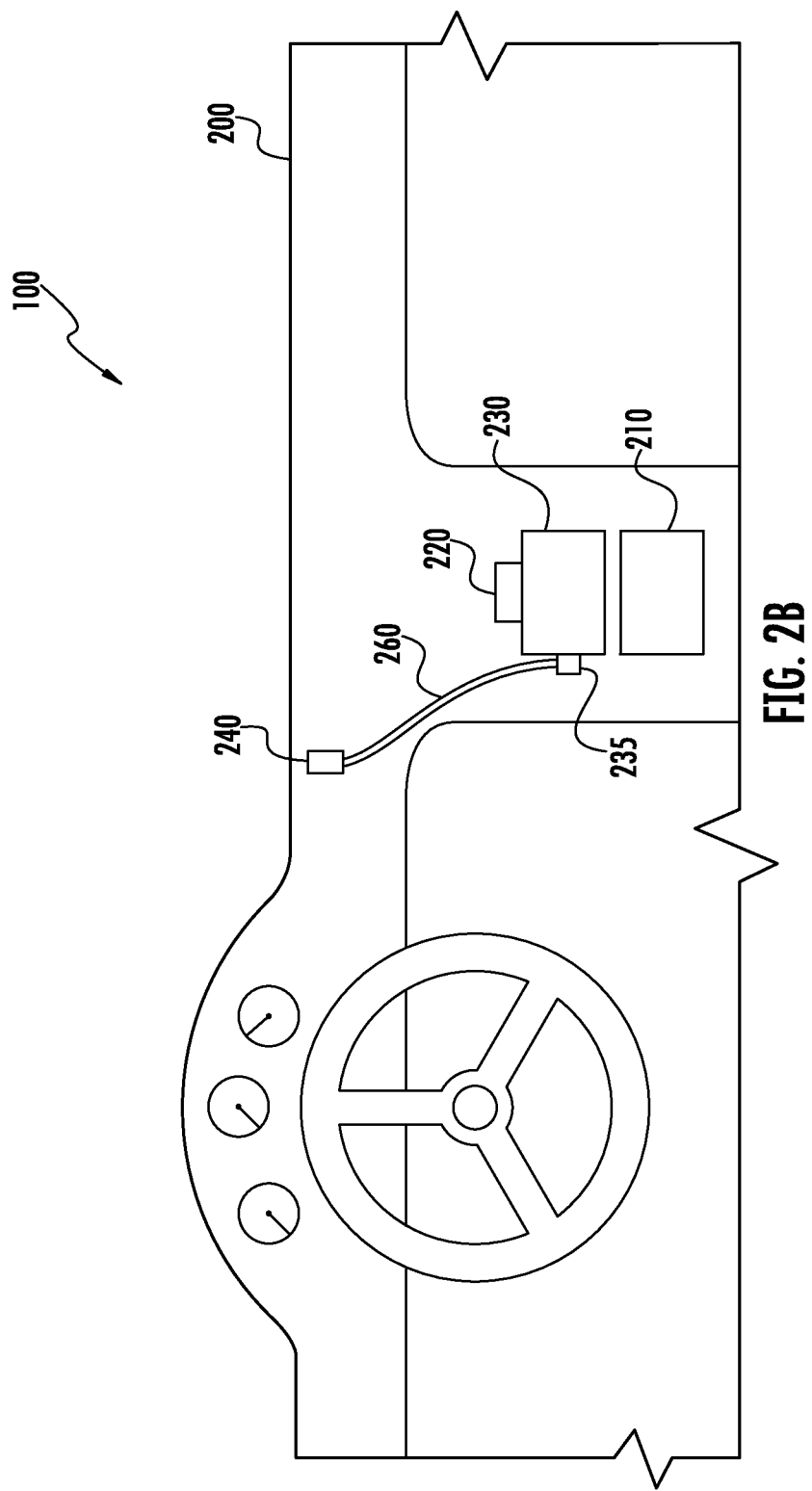

ROBOTIC VEHICLE CONTROL

CROSS-REFERENCE TO RELATED APPLICATION

This application is a continuation of U.S. patent application Ser. No. 14/091,060, filed Nov. 26, 2013, entitled "ROBOTIC VEHICLE CONTROL," which is incorporated herein by reference in its entirety.

BACKGROUND

With the general population increasing and vehicles becoming cheaper and easier to obtain, the number of people on roadways has increased. As roadways become more crowded, the likelihood of accidents increases. However, technology has also advanced, leading to an increase in vehicle safety features, which can limit the severity and frequency of such vehicular accidents.

SUMMARY

One embodiment relates to a vehicle comprising a detection system configured to acquire data regarding operation of the vehicle. The vehicle also includes a robotic driving device configured to provide robotic control of the vehicle. The vehicle further includes a control system configured to determine that the robotic driving device is activated, such that the vehicle is in a robotic driving mode; receive a request by a prospective operator of the vehicle to deactivate the robotic driving device to initiate a manual driving mode; determine whether the prospective operator is impaired based on the data; and selectively deactivate the robotic driving device based on the determination.

Another embodiment relates to an apparatus for detecting and responding to a potential impairment of an operator of a vehicle, comprising a detection system configured to acquire data regarding the operator during constrained operation of the vehicle. The apparatus also includes a robotic driving device configured to provide robotic operation of the vehicle during the operator's constrained operation of the vehicle. The apparatus further includes an evaluator configured to evaluate the operator during the operator's constrained operation for an impairment based on the data. The apparatus also includes a control system configured to selectively deactivate the robotic driving device based on signals received from the evaluator.

Still another embodiment relates to an apparatus for detecting and responding to an emergency situation in a vehicle, comprising a detection system configured to acquire data regarding operation of a vehicle. The apparatus also includes a robotic driving device configured to provide robotic operation of the vehicle. The apparatus further includes a control system configured to determine whether an emergency situation exists based on the data and based on the determination, to selectively activate the robotic driving device to direct the vehicle to an emergency response location selected based on the emergency situation.

Yet another embodiment relates to a method for detecting and responding to operator impairment in a vehicle comprising acquiring data regarding a prospective operator, receiving a request from the prospective operator to initiate a manual driving mode, determining that a robotic driving device is activated, determining whether the prospective operator is impaired based on the data, and selectively deactivating the robotic driving device based on the determination.

Still another embodiment relates to a method of analyzing an operator of a vehicle for impairment, comprising acquiring data regarding the operator during constrained operation of the vehicle, activating a robotic driving mode during the operator's constrained operation of the vehicle, receiving a driving command from the operator during the operator's constrained operation, evaluating whether the operator is impaired during the operator's constrained operation based on at least one of the data and the received driving commands, and selectively deactivating robotic driving mode based on the evaluation.

Another embodiment relates to a method of responding to an emergency situation in a vehicle, comprising receiving threshold data indicative of an emergency situation, acquiring operation data regarding operation of the vehicle, determining whether an emergency situation exists based on at least one of the threshold data and the operation data, and selectively activating a robotic driving mode to direct the vehicle to an emergency response location selected based on the emergency situation determination.

Still another embodiment relates to an impaired driving avoidance system, comprising a detection system configured to acquire data regarding an operator of a vehicle and a control system coupled to the detection system including an evaluator. The control system is configured to determine whether the operator is impaired based on the data, determine that a robotic driving device is activated such that the vehicle is in a robotic driving mode, receive a request to deactivate the robotic driving device, and selectively deactivate the robotic driving device based on the determination of whether an impairment exists. The evaluator is configured to constrain control of the vehicle and provide an operator with an evaluation period within which to show that the operator is not impaired.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 2B is a front view of a vehicle's dashboard including wired protocols, according to one embodiment.

DETAILED DESCRIPTION

Figure 1:
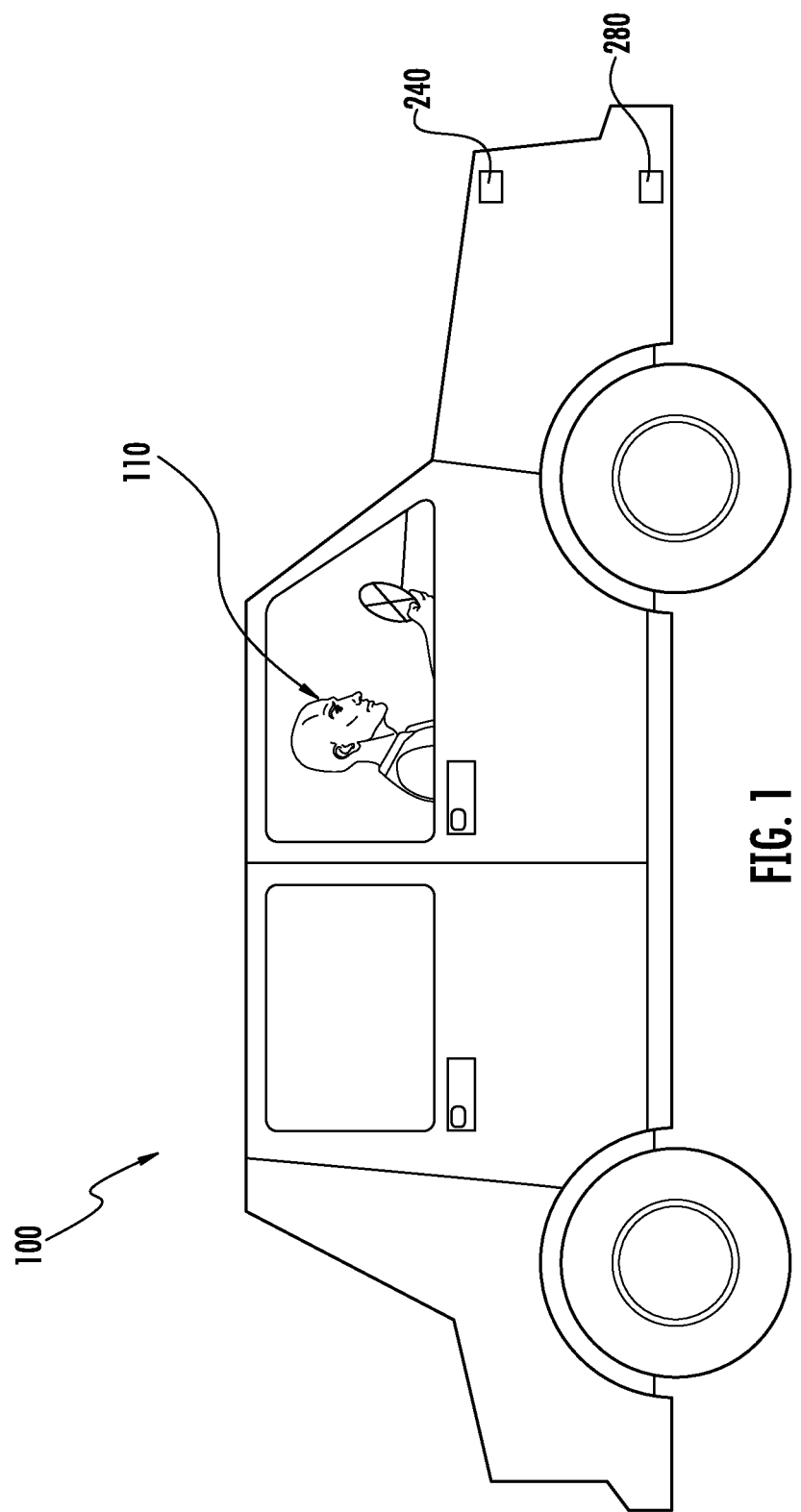
FIG. 1 is an isometric view of a vehicle and an operator, according to one embodiment.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to the figures generally, various embodiments disclosed herein relate to a vehicle with two driving modes: manual and robotic. Manual driving mode relates to driver-controlled vehicle operation and robotic driving mode relates to autonomous vehicle operation. Implementation of robotic driving mode is configured to be in connection with detection and analysis of an operator's characteristics. These characteristics include his/her driving characteristics and/or state characteristics, such as a presence of alcohol in one's system. If an impairment or potential impairment is detected based on the operator's characteristics, robotic driving mode is activated, wherein the vehicle can be autonomously driven to various locations, including hospitals, if an emergency is detected. As discussed in greater detail below, various techniques may be utilized in determining when and how to activate robotic driving mode. It should be understood that the present disclosure relates to various vehicles, including automatic and/or manual transmission cars, trucks, semi-trucks, buses, motorcycles, three-wheeled motorcycles, boats, trains, etc.

Referring to FIG. 1, vehicle 100 with operator 110 is shown according to one embodiment. In traditional vehicles, operator 110 is responsible for starting vehicle 100, choosing where to drive vehicle 100, and driving vehicle 100. This type of vehicle operation will be referred to as manual driving (or, manual driving mode) herein. It should be understood that operator 110 is not included in FIGS. 2A-2B for clarity, but will be referred to as if present.

Figure 2A:
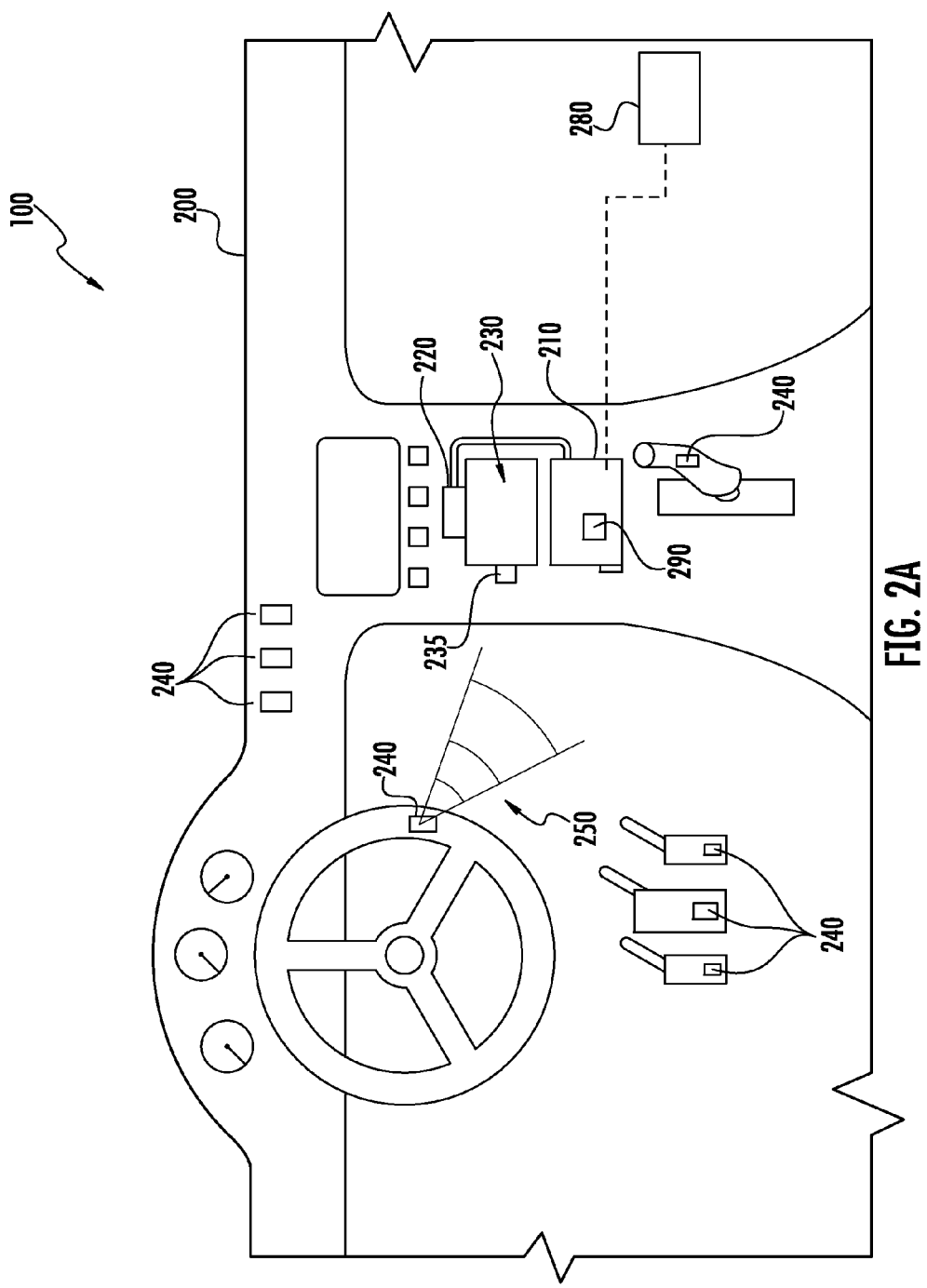
FIG. 2A is a front view of a vehicle's dashboard including a robotic driving device, a control system, and a detection system, according to one embodiment.

Referring to FIG. 2A, a front view of dashboard 200 and other components of vehicle 100 is shown according to one embodiment. Vehicle 100 includes robotic driving device 210, control system 220, and detection system 230. Detection system 230 includes one or more sensors shown as sensor 240, which can be configured to acquire various types of data. Detection system 230 further includes receiver 235. Receiver 235 is configured to receive the data acquired by sensor 240. In one embodiment, receiver 235 then transmits this data to control system 220 for further processing.

According to one configuration, receiver 235 and sensor 240 communicate via wireless protocols 250. Wireless protocols can include Wi-Fi, wireless local area network ("WLAN"), Bluetooth, radio frequency ("RF"), optical communication, infrared, microwave, sonic and ultrasonic waves, and electromagnetic induction communications platforms. According to an alternative embodiment, receiver 235 and sensor 240 communicate via wired protocols, such as a wired connection 260 (see FIG. 2B). Wired protocols can include fiber-optics, universal serial bus ("USB"; including all micro, mini, and standard types), twisted-pair cables, and coaxial cables.

Sensor 240 is configured to acquire data related to driving characteristics of operator 110, state characteristics of operator 110, and/or surroundings data, which includes environmental conditions both inside and outside of vehicle 100. According to one embodiment, sensor 240 can be placed inside and/or outside of vehicle 100. Sensor 240 can also be configured to directly attach to operator 110. In the alternative, sensor 240 is configured to operate without direct attachment to operator 110.

Figure 3:
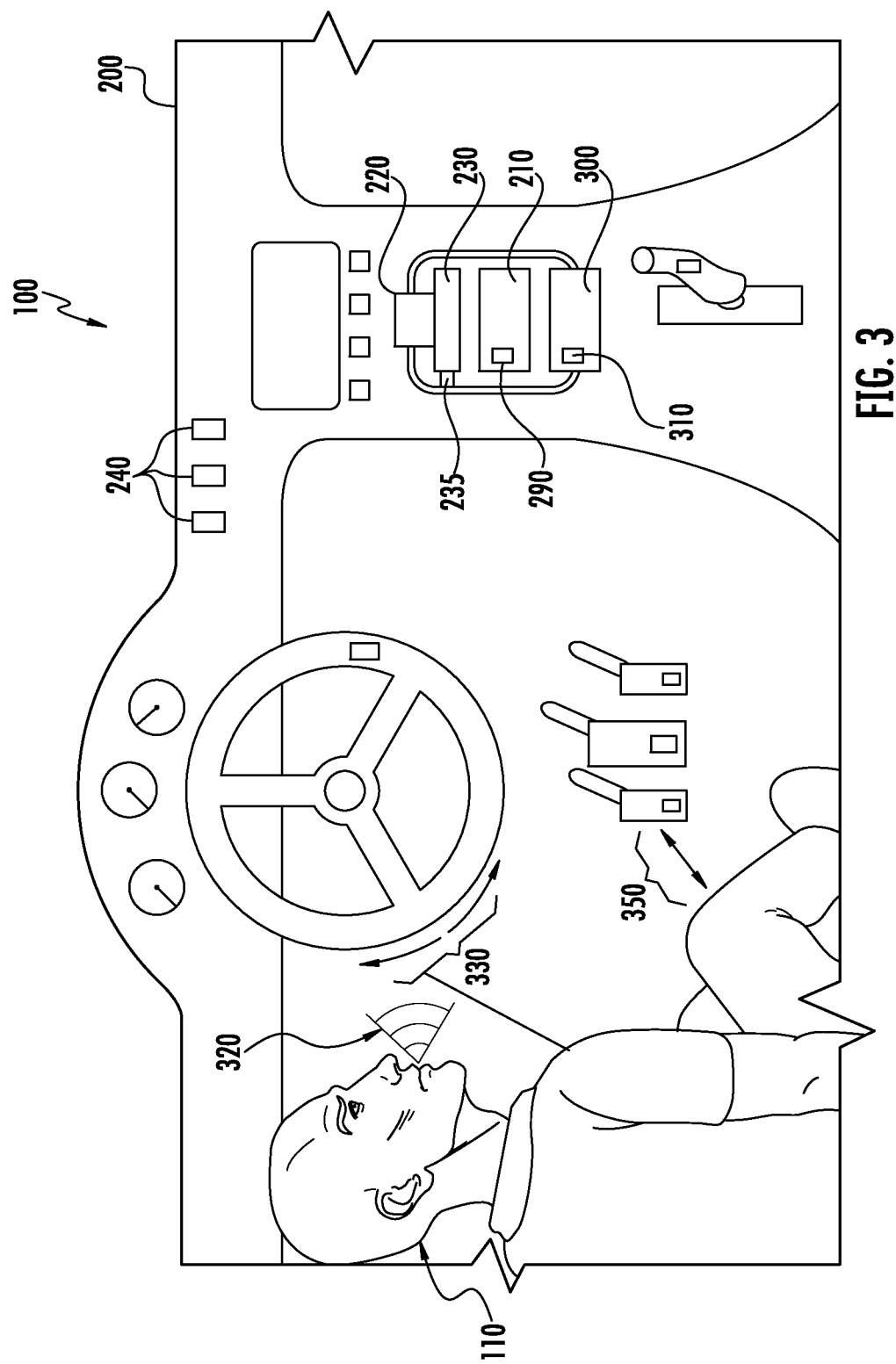
FIG. 3 is a front view of a vehicle's dashboard including a robotic driving device, a control system, a detection system, and an evaluator, according to one embodiment.

Sensor 240 can include external vehicle sensors, such as: seismometers; geophones; carbon monoxide and carbon dioxide detectors; smoke detectors; radiation detectors; etc. Sensor 240 can also include internal vehicle sensors, such as: carbon monoxide and carbon dioxide detectors; smoke detectors; radiation detectors; odorant sensors (e.g., for alcohol, marijuana, etc.); drug and alcohol sensors; accelerometers; pressure gauges on the steering wheel, shifter, and brake, accelerator, and clutch pedals; and temperature and pressure sensors. Sensor 240 can further include breathalyzers; other drug and alcohol sensors (e.g., pupil dilation sensor); vision and hearing sensors; alertness sensors; heart rate monitors; blood analyzers; tremor sensors (e.g., to detect hand tremors); dexterity sensors; cognitive sensors; etc. In some embodiments, an operator is nominally impaired (e.g., due to poor eyesight, poor hearing, a medical condition such as Parkinson's, bipolar disorders, or the like) and requires active measures to sufficiently reduce the impairment in order to safely operate the vehicle. In this embodiment, sensor 240 can detect (e.g., via cameras, blood analyzers, communication with drug dispensers, etc.) the presence or absence of eyeglasses, contact lenses, hearing aids, drugs for treating the impairing medical condition (i.e., the presence of an impairment antagonist drug), etc. In some embodiments, sensor 240 is configured as an external sensor to detect toxins in the environment that may impair the operator, such that robotic driving device 210 may be activated. It should be understood that all of the above-mentioned sensors can be used in conjunction with each other or independent of each other. Moreover, FIGS. 1-3 are illustrative and not meant to be limiting as to various sensor 240 locations.

As mentioned above, data acquired can include state and driving characteristics of operator 110 and surroundings data. State characteristics can include an indication of: alertness; pupil-dilation; presence of impairing drugs (e.g., lysergic acid diethylamide, marijuana, etc.); temperature; response to test questions; speech patterns; blood-alcohol level; medical diagnostics, such as heart rate, blood flow, and oxygen levels; vision acuity; cognitive response ability; etc. Driving characteristics of an operator can include an indication of: shifting tendencies; squeeze pressure on shifter and steering wheel; jerkiness of steering; frequency and force of applying brakes; rate and force of clutch and accelerator pedal depressions/releases; lane changing tendencies; following distance tendencies (e.g., average); pattern of obeying posted driving laws; poor driving skills; etc. Surroundings data can include an indication of: environmental conditions both internal and external of the vehicle, such as: temperature and pressure levels; carbon monoxide, carbon dioxide, smoke, and radiation levels; presence and level of harmful toxins; icy road conditions; time of day (e.g., nighttime); ambient light levels (e.g., night, glare, dusk); presence of fog; precipitation (e.g., rain, hail, snow); etc.

Sensor 240 transmits the acquired data to detection system 230. Detection system 230 is configured to transmit the data to control system 220. Control system 220 is configured to receive the data and analyze it for operator 110 impairment and/or potential impairment.

Control system 220 is further configured to activate robotic driving device 210 and to receive a request (e.g., to operate the vehicle in manual driving mode) from an operator or prospective operator. According to one configuration, during a period of robotic driving, control system 220 receives a request from a prospective operator to take over control of the vehicle (i.e., deactivate the robotic driving device 210). The request can include a selection by the prospective operator or a command to deactivate a robotic driving mode in favor of a manual driving mode; this selection may be verbal, electronic, touching of a switch, etc. According to one configuration, control system 220 can also receive operator inputs (e.g., data values corresponding to no impairment) defining approved data levels for manual driving mode (i.e., data levels corresponding to no impairment). Approved data levels may also be set by a manufacturer and/or by federal, state, and local law agencies. As mentioned above, control system 220 can be configured to analyze data acquired by sensors 240. Data can be acquired before the request, and/or in response to it. If the acquired data does not conform to the approved and/or pre-selected data levels (can be based on one or many data points), control system 220 prevents deactivation of robotic driving device 210. For example, prospective operator 110 may be too tired to safely operate the vehicle. Sensor 240 may detect a slow cognitive response time of prospective operator 110 (e.g., prospective operator slowly, incorrectly, or altogether does not respond to test questions), and based on this data, control system 220 may prevent deactivation of robotic driving device 210, thereby preventing prospective operator 110 from controlling vehicle 100 (e.g., via manual driving mode). Alternatively, sensor 240 may detect carbon monoxide outside of vehicle 100, such that control system 220 retains robotic driving device 210 in anticipation of a potential driver impairment. Detection of carbon monoxide may qualify as a potential impairment depending on how control system 220 is pre-programmed. As such, this type of potential impairment (e.g., elevated levels of carbon monoxide, elevated levels of radiation, presence of tear gas, etc.) may also prevent deactivation of robotic driving device 210 to prevent the possibility of impaired operator driving.

Defining when an impairment exists can be highly customizable and/or programmable. For example, any acquired data could be required to be within ten percent of set parameter numbers/approved data levels; within a standard deviation from an average of acquired data levels; within a certain amount of approved/pre-programmed data levels; not exceeding (alternatively, below) thresholds for certain data characteristics; etc. Additionally, the operator may be required to input his/her characteristics (e.g., age, height, weight, blood type, health history, etc.), such that the impairment determination is tailored for a specific operator. For example, a larger individual may be able to consume more alcohol than a smaller person before becoming impaired, such that this correlation is now taken into account. An operator, a user, and/or a manufacturer can also program control system 220 with their own formula, method, and/or rubric for what qualifies as an impairment. This programming can be based on federal, state, or local laws. In turn, what constitutes an impairment in one state may not qualify as an impairment in another state, such that programming may be location-specific (e.g., state-based, county-based, etc.).

According to another embodiment, data acquired by sensor 240 is stored by control system 220 for each operator and prospective operator of vehicle 100. As such, many vehicle operators and prospective operators can be analyzed for impairment based on his/her average data levels or other driver-specific parameters. In another embodiment, average data levels are not used to determine impairment. The acquired data is analyzed against preset/pre-approved data levels; or with a preset algorithm; and/or with any of the methods listed above.

In another embodiment, sensor 240 is configured to detect and acquire data regarding emergency situations. Emergency situations can include an indication of a presence of excessive blood loss; loss of consciousness; presence of potentially lethal fumes, such as carbon monoxide; going into labor; a medical emergency; low heart rate; presence of a harmful drug in the operator; presence of radiation; theft of vehicle; etc. For example, detection of an unfamiliar operator based on facial recognition may be considered an emergency situation by control system 220. Robotic driving device 210 may then be activated, and vehicle 100 re-routed to a police station. Additionally, the police, owner of vehicle 100, and other emergency service personnel may be contacted. Operator 110 and/or the manufacturer may also have the option of using control system 220 to dictate when emergency situations exist. For example, if operator 110 has a blood alcohol content over 0.08% (0.08 grams of alcohol per 100 milliliters of blood), control system 220 may consider him/her impaired and activate robotic driving device 210. If operator 110 has a blood alcohol content greater than 0.25% (0.25 grams of alcohol per 100 milliliters of blood), control system 220 may consider this to be an emergency situation, and activate emergency response protocols. Control system 220 is configured to be programmed with parameters indicative of various emergency situations, such that the data acquired by sensors 240 can be analyzed for emergency situations.

Emergency response protocols can include re-routing vehicle 100 via robotic driving mode to the nearest appropriate emergency response location (e.g., medical facility for a medical emergency, law enforcement facility for theft of the vehicle, etc.) based on the nature of the emergency situation detected. Moreover, the appropriate emergency response location can be selected by an operator after an emergency is detected, selected by off-site personnel in response to an emergency detection, and/or selected and programmed into control system 220 prior to any emergency situation being detected (i.e., if a medical emergency occurs, the pre-selected emergency location of a hospital is selected by pre-programming where the vehicle is then directed to the hospital via robotic driving mode). In another embodiment, the emergency response location can be selected based on distance (e.g., nearest location), wait time (i.e., if one hospital is closer but has a longer wait time than a second hospital, the first hospital is bypassed), insurance provider of the operator or prospective operator (i.e., only directing the vehicle to locations covered by the operator's insurance), specialty of the location (e.g., a police station for a theft or a hospital that handles child births versus one that does not), or some combination therewith. Emergency response protocols can also include activating robotic driving device 210 to otherwise control vehicle 100; alerting the appropriate personnel; turning off vehicle 100 upon arrival at the appropriate emergency response location; etc. Emergency response protocols can be pre-programmed by a manufacturer in control system 220 and/or modified by operator 110 and/or by other vehicle 100 users. Additionally, vehicle 100 may be controlled via robotic driving device 210 by offsite emergency personnel in order to divert vehicle 100 to a proper location.

Further referring to FIG. 2A, robotic driving device 210 is configured to drive vehicle 100. As such, robotic driving device 210 is coupled to the steering, electrical, transmission, and engine components in a vehicle. Robotic driving device 210 is also configured to obey all posted signage and all federal, state, and local vehicular laws. Robotic driving device 210 can include a transceiver 280. Transceiver 280 is configured to acquire vehicle surroundings information or data. Vehicle surroundings information can include an indication of: the presence and location of other vehicles; posted speed limits; weather conditions; etc. Robotic driving device 210 uses this information to safely and effectively drive vehicle 100. Robotic driving device 210 can also include a navigation system shown as global positioning system ("GPS") receiver 290. GPS receiver 290 is configured to acquire various location information. This information is configured to aid vehicle 100 in going to a specific location while using robotic driving device 210. Robotic driving device 210 is configured to drive and navigate vehicle 100: along a pre-programmed path provided by control system 220 whenever robotic driving device 210 is activated; along a path provided by a prospective operator; along a path provided by operator 110 while in vehicle 100 (in either robotic driving mode or manual driving mode); and/or to a location being driven to by operator 110 prior to robotic driving device 210 being activated. According to another configuration, robotic driving device 210 is capable of being controlled remotely by a central operator and/or by a central processing unit offsite.

According to one embodiment, after vehicle 100 is started, vehicle 100 cannot be operated (e.g., manual driving mode) without an impairment determination being made. In some embodiments, only state characteristics and/or surroundings data are used because the vehicle is not moving. According to another embodiment, the vehicle is able to be started and driven in manual driving mode prior to the impairment determination taking pace. Preset parameters in control system 220 can determine how long the vehicle can be driven without engaging in an impairment analysis. According to an alternative embodiment, the vehicle is started in robotic driving mode, operated in robotic driving mode, and then an operator impairment analysis is made.

In some embodiments, an evaluator can be used to evaluate an operator while the vehicle is in motion. For example, referring to FIG. 3, evaluator 300 coupled to vehicle 100 is shown according to one embodiment. Evaluator 300 is configured to provide operator 110 with constrained operational control of the vehicle and an evaluation period during which the operator or prospective operator has the opportunity to show that he/she is not impaired. At the completion of the evaluation period or at some point prior, evaluator 300 is configured to send one or more signals to control system 220 regarding the results of the evaluation (i.e., whether the operator is impaired and/or should be in control of the vehicle). If operator 110 is successful (shows no impairment), control system 220 can deactivate robotic driving device 210 in favor of manual driving mode.

According to one embodiment, evaluator 300 is configured to be utilized while vehicle 100 is using robotic driving device 210 (e.g., while the vehicle is in motion with robotic driving mode). During the evaluation period, evaluator 300 is configured to receive driving commands from operator 110. In this embodiment, vehicle 100 stays in robotic driving mode while receiving commands from operator 110, such that operator 110 has only constrained operational control over vehicle 100. In this embodiment, evaluator 300 (alternatively, control system 220) can review operator commands, and can compare the effects (e.g., actual or predicted effects) of operator commands to the effects of the robotic driving device's commands. If the effects differ too much (e.g., beyond a defined threshold) evaluator 300 can send a signal to control system 220 to ignore operator commands in favor of those from robotic driving device 210. Conversely, if the effects are sufficiently similar, the operator's commands can be accepted.

In some embodiments, evaluator 300 (alternatively, control system 220) can apply a weighted combination of commands from the operator and from the robotic driving device. In another embodiment, driving commands of operator 110 are able to override robotic driving device 210 during the constrained operation period. However, if operator 110 displays an impairment, operator 110 will no longer be able to drive, steer, or control vehicle 100 and robotic driving device 210 will override the driving commands from operator 110. For example, if operator 110 makes too many or too great of mistakes (e.g., deviates from the driving lane) during the constrained operation period, evaluator 300 can stop the evaluation period and return to robotic driving mode.

Driving commands can include rate, frequency, and force of depression and release in brake, accelerator, and clutch pedals (350). Driving commands can also include verbal instructions 320 received from operator 110, such as "go faster," "turn right," "slow down," etc. Driving commands can further include frequency and force of turning the steering wheel (330). After receiving the driving commands, evaluator 300 is configured to analyze the commands for impairment. For example, if operator 110 instructs vehicle 100 verbally 320 to "go faster" while at a red stop light, evaluator 300 will send a signal to control system 220 instructing control system 220 that operator has not successfully completed the evaluation. As such, control system 220 will keep vehicle 100 in robotic driving mode due to the appearance of an operator impairment. In an alternative embodiment, evaluator 300 is configured to transmit operator driving commands to control system 220, such that control system 220 can be configured to analyze the commands for impairment rather than evaluator 300.

According to another embodiment, evaluator 300 is further configured to analyze/evaluate data regarding operator 110 (or prospective operator) of vehicle 100. The data can include state and driving characteristics as well as surroundings data, as described above. The data can be continuously acquired while operator 110 is in vehicle 100 or at specific intervals of time (e.g., every five minutes while the vehicle is in operation). If evaluator 300 determines that the data indicates no impairment, evaluator 300 can send a signal to control system 220 to deactivate robotic driving device 210 in favor of manual driving mode.

According to another embodiment, evaluator 300 includes a timer 310. Timer 310 is configured to control the length of time of the evaluation period or the constrained operation period. Timer 310 is further configured to control the length of time between evaluation periods. For example, the time between evaluation periods can be pre-programmed, such as forty-five minutes. In turn, operator 110 may have multiple opportunities to be evaluated while in vehicle 100. In some embodiments, timer 310 may be programmed with a three minute evaluation period, such that operator 110 is evaluated and in control (or, alternatively, just evaluated with no vehicle control) of vehicle 100 for three minutes. In an alternative embodiment, the length of the evaluation period can be based on driving activity, such as the number of turns taken; different speeds achieved; number of stop-to-go transitions; or any other metric wherein the driving commands and/or state characteristics of operator 110 are evaluated. Timer 310 is highly programmable, with a user, operator, and/or manufacturer being able to set the evaluation period length and/or time between the evaluation periods (e.g., through control system 220).

Figure 4:
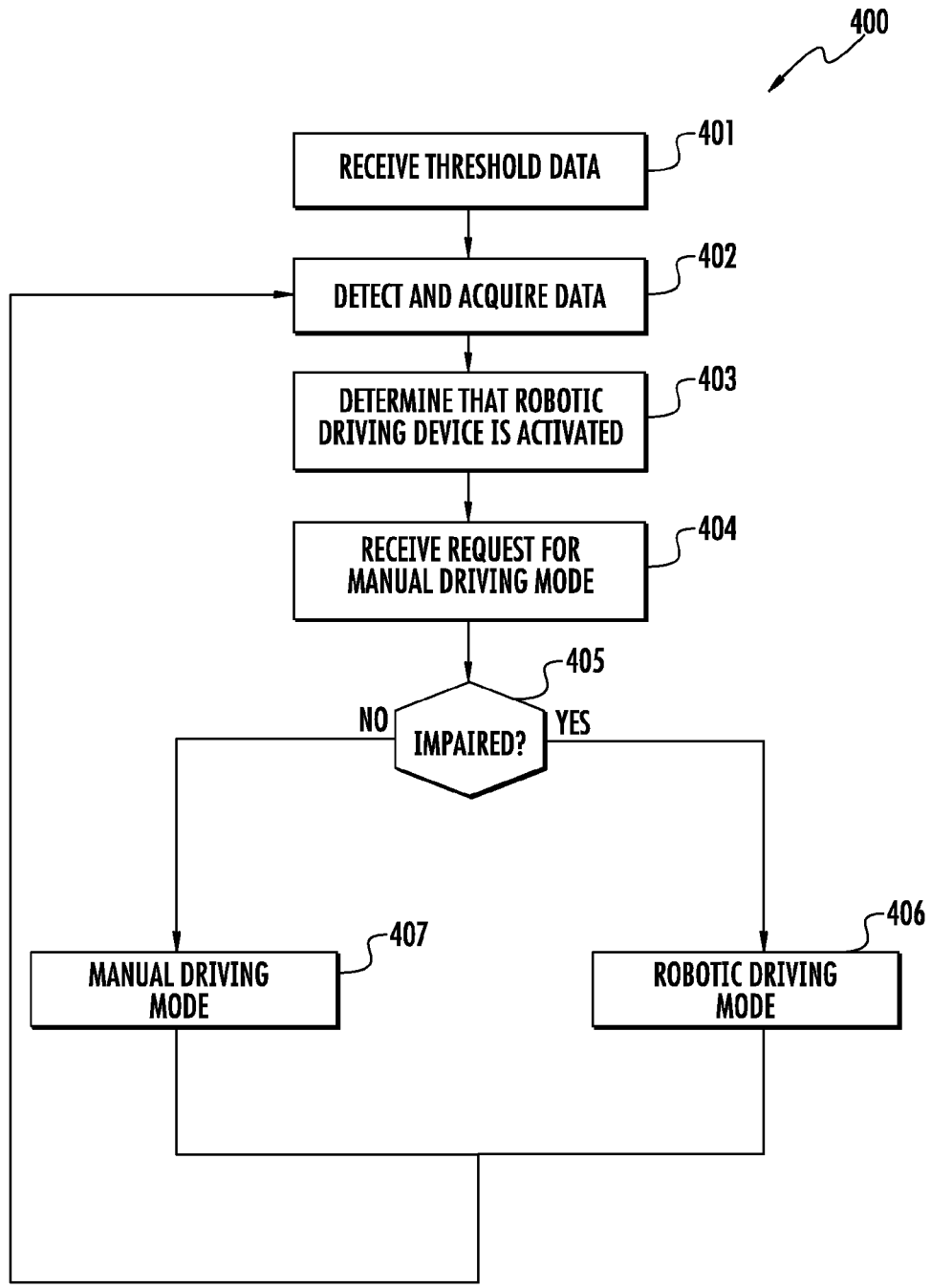
FIG. 4 is a diagram of a method of detecting and responding to driver impairment, according to one embodiment.

Referring next to FIG. 4, method 400 for detecting and responding to operator impairment in a vehicle is shown according to one embodiment. Pre-approved/selected threshold data levels are received by a control system (401). Threshold data includes approved operator state characteristics, such as an indication of: blood-alcohol level; presence of harmful affecting drugs; medical diagnostics, such as heart rate and oxygen levels; vision acuity; and cognitive reactiveness acuity (see above for additional data references). Threshold data can also include pre-approved/selected operator driving characteristics (see above) and/or pre-approved/selected surroundings data (see above, e.g., environmental conditions internal and/or external to the vehicle). Pre-approved/selected threshold data levels can be inputted by any operator of the vehicle, the vehicle's owner, and/or be preset from manufacturer specifications. Operator (and prospective operator) and/or surroundings data is acquired by a detection system using a sensor (402). The sensor can include the sensor types and functions described above. A robotic driving device is determined to be activated (403). As such, the vehicle is in robotic driving mode. A request from the operator or prospective operator to initiate manual driving mode is received (404). Typically, a control system receives the request from a prospective operator to take over control of the vehicle (i.e., deactivate the robotic driving device 210). The request can include selection by the prospective operator or a command to deactivate a robotic driving mode for a manual driving mode; this selection may be verbal, electronic, touching of a switch, etc. For example, the user can start the vehicle (i.e., turn the key) and attempt to put the vehicle into gear, which is a "request" to initiate manual driving mode.

The operator and/or surroundings data is transmitted to the control system and processed alongside the pre-approved/selected threshold data levels to determine whether the operator (or prospective operator) is impaired or potentially may be impaired (405). Based on this determination, the request may be granted or refused by the control system. If the control system determines the operator to be impaired or potentially impaired, the request is refused, which thereby initiates robotic driving mode (406). Thus, the control system has selected to not deactivate the robotic driving device. Robotic driving device can have the same function and characteristics as described earlier. If the control system determines that the operator is not impaired, the request is granted, which initiates manual driving mode (407). Thus, the robotic driving device is deactivated, which in turn initiates manual driving mode. According to another embodiment, the acquired data could be stored for one or more operators to be used for subsequent impairment determinations.

The detection system can be programmed to continuously or periodically acquire operator and/or surroundings data. For example, if the operator was previously determined to be impaired, during a later analysis period, the control system may determine that the operator is no longer impaired and deactivate robotic driving mode. Additionally, operator and/or surroundings data can be continually or periodically acquired while in manual driving mode. If an impairment is determined at some point during the operation of the vehicle, robotic driving device can be activated.

Figure 5:
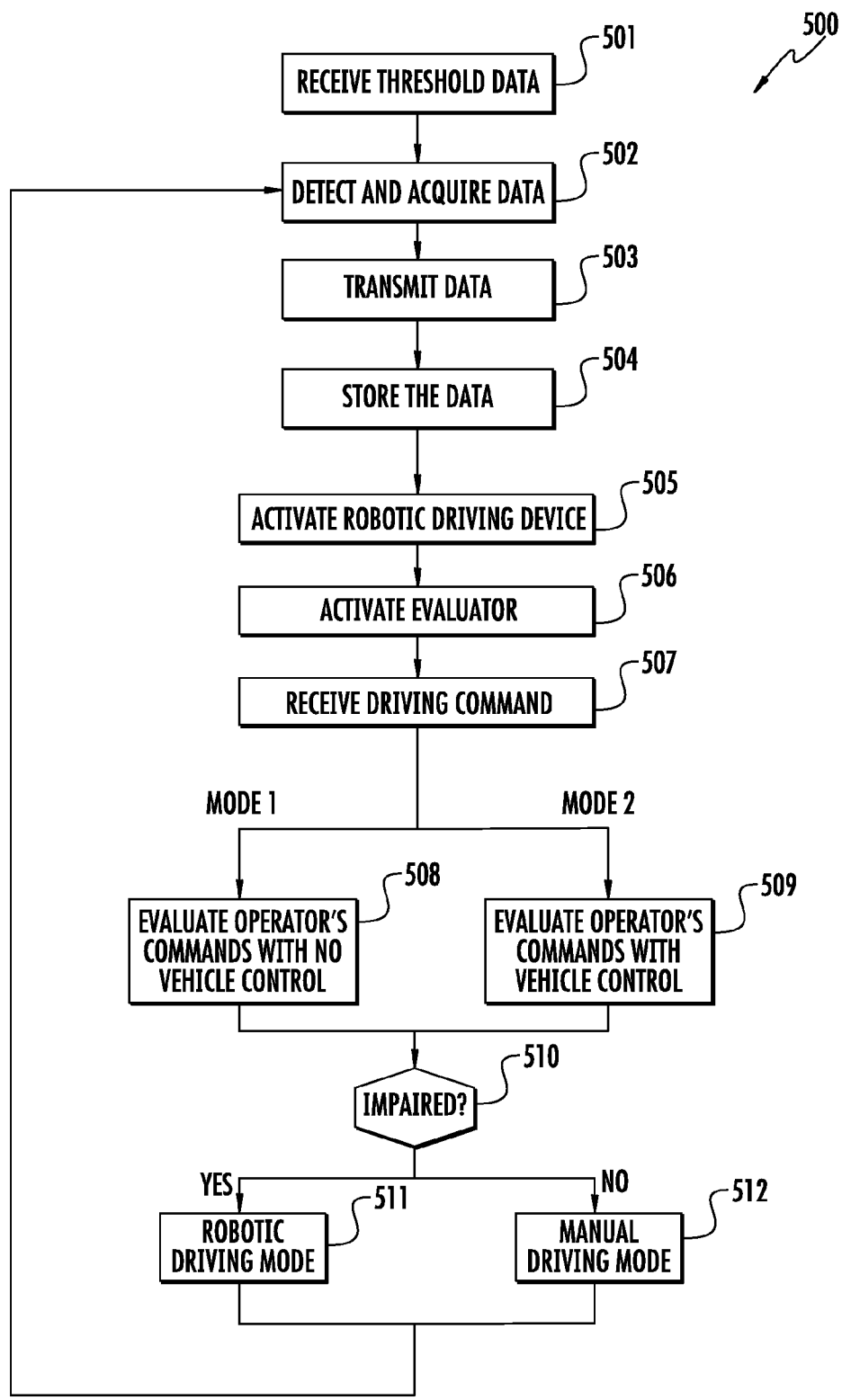
FIG. 5 is a diagram of a method of activating a robotic driving device based on evaluating an operator, according to one embodiment.

Referring next to FIG. 5, method 500 of initiating robotic driving mode using an evaluator is shown according to one embodiment. Pre-approved/selected threshold data levels of a vehicle operator are received by a control system (501). Pre-approved/selected threshold data levels are mentioned above and can be inputted by any operator of the vehicle, the vehicle's owner, and/or be preset from a manufacturer. Operator (i.e., driving and state characteristics) and/or surroundings data is acquired by a detection system using a sensor (502). The operator and/or surroundings data is transmitted to the control system (503), and stored in the control system of the vehicle (504). This can be done, for example, to acquire average data levels of each operator, if there are several operators of the vehicle. Thus, the pre-approved/selected threshold data levels can be based on each operator's average acquired data levels. For example, a high pupil dilation may signify impairment in one operator wherein that pupil dilation is normal in another operator (no impairment). A robotic driving device is activated by the control system (505). The robotic driving device can have the same function and characteristics as described above. The control system then activates an evaluator to evaluate the operator during a constrained operational period of control of the vehicle by the operator (506). The evaluator is configured to receive driving commands from the operator or prospective operator of the vehicle during the constrained period (507). As mentioned above, operator commands can include verbal instructions on driving the vehicle and/or physical commands, such as actually steering and using the accelerator pedals.

Upon activating the evaluator, two modes are possible. Based on initial programming, a default mode of the evaluator is initially selected (e.g., mode 1). However, the control system can allow a user, manufacturer, or operator to change which mode the evaluator is in. If the evaluator is activated in mode 1, the evaluator analyzes and evaluates the commands of the operator (or prospective operator) with such commands having no control over the operation of the vehicle (508). If a user has directed the control system to change the evaluator to mode 2, then the evaluator is used to analyze and evaluate the commands of the operator with such commands actually controlling the operation of the vehicle (509). For example, the operator may verbally direct the vehicle by saying "turn" and "speed up," whereby the vehicle then "turns" or "speeds up." However, if the evaluator determines that the commands show the operator to be impaired, then the commands no longer control the vehicle and robotic driving mode is reengaged (hence, constrained operational control of the vehicle).

Regardless of whether mode 1 or mode 2 is active, the time frame within which the operator's commands (e.g., verbal, physical, etc.) are analyzed is referred to as the evaluation period (or constrained operation period) herein. At the end of the evaluation period, the evaluator analyzes the commands for impairment (510). If the operator is determined/evaluated to be impaired, robotic driving mode is reengaged (511) if in mode 2 via activation of the robotic driving device (note that robotic driving mode is already active in mode 1). If the operator is evaluated to not be impaired, the robotic driving device is deactivated in favor of manual driving mode (512). According to one embodiment, this method can be continually performed while the car is in operation.

According to one configuration, evaluation of the commands for operator impairment (510) can be done by comparing the current operator commands with pre-approved commands. The control system can use the acquired data (steps 501 through 504) to determine what the appropriate operator commands should be based on the, for example, surroundings data. The operator's commands can then be analyzed against the determined appropriate commands for impairment. According to another embodiment, the evaluator can compare the pre-robotic driving mode commands from past operator experiences with current commands to determine if there is a deviation that shows operator impairment (e.g., if an operator drives the same road weekly at 25 miles per hour, and during evaluation drives the road at 75 miles per hour while swerving, this deviation may indicate impairment). Additionally, a safety factor identifying an acceptable difference between the operator commands and the approved commands can be utilized to determine operator impairment.

According to another embodiment, a timer is included with the evaluator. The timer is configured to preset the time for the evaluation period. The timer is further configured to set the time between evaluation periods. In an alternative embodiment, the evaluation period may be based on driving activity, such as the number of turns taken; different speeds achieved; number of stop-to-go transitions; or any other metric wherein the driving commands and/or state characteristics of the operator are evaluated.

Figure 6:
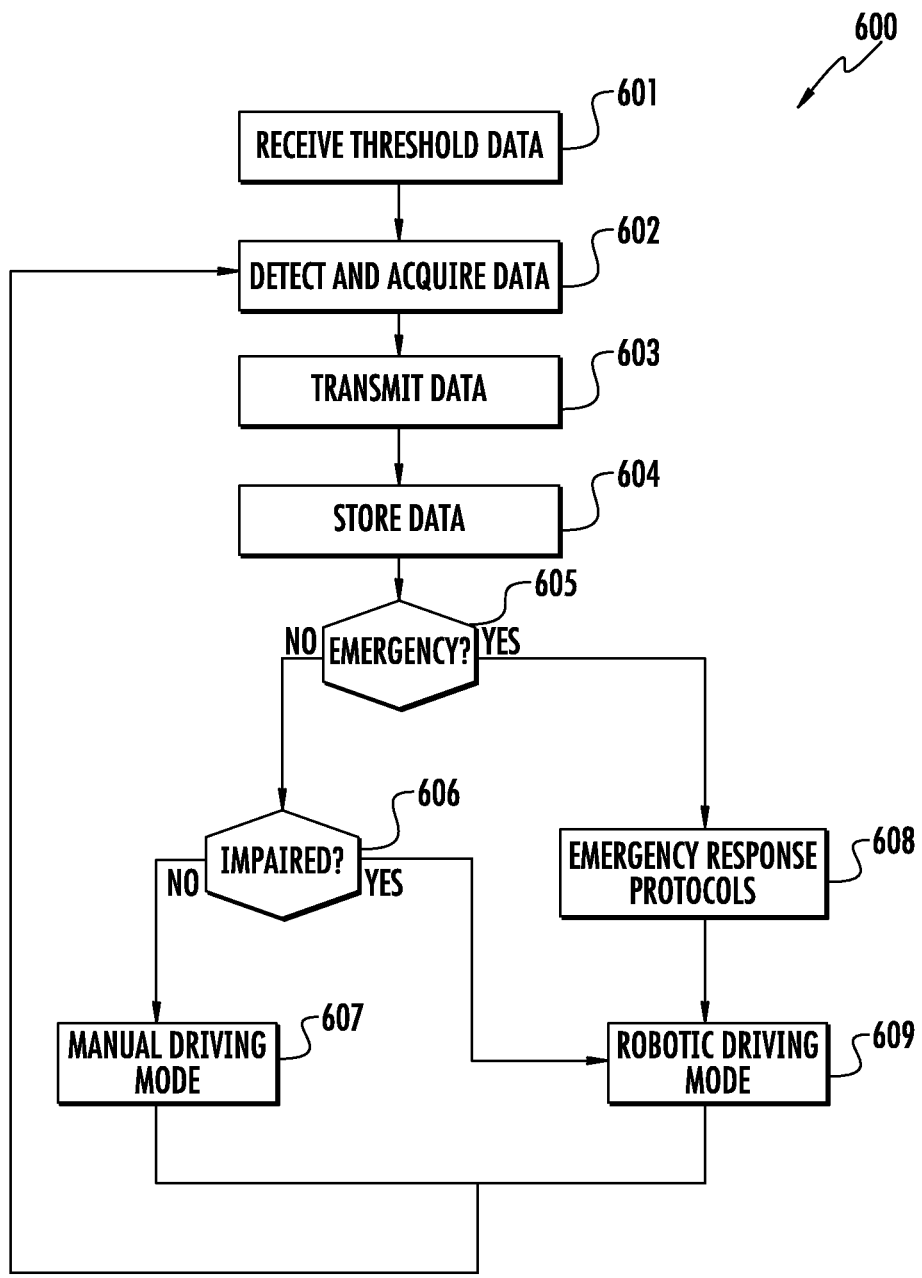
FIG. 6 is a diagram of a method of initiating a robotic driving device based on an emergency, according to one embodiment.

Referring to FIG. 6, method 600 for operating a vehicle with a robotic driving mode and an emergency response feature is shown, according to one embodiment. Approved/pre-selected data levels are received by a control system (601). The threshold data levels may include operation data including operator state and driving characteristics as well as surroundings data. The data levels may also include threshold parameters indicative of various emergency situations. A detection system uses a sensor to detect and acquire threshold and operation data (602). The acquired data is then transmitted back to the control system (603) and stored in the control system (604). This allows for computation of average acquired data levels for each operator and average threshold data levels (e.g., sunlight only present for 4 hours a day in one area of the world may not indicate an emergency but may indicate an emergency in another area of the world based on threshold data averages) Subsequently, impairment determinations can be made based on the averages (or, alternatively, based on a pre-programmed formula, rubric, or algorithm). The data (threshold and operational) is analyzed for the presence of any emergency situations (605). Emergency situations can include an indication of a presence of excessive blood loss; loss of consciousness; presence of potentially lethal fumes, such as carbon monoxide; going into labor; medical emergency; low heart rate; presence of a harmful drug in the operator; presence of radiation; theft of vehicle; etc. If there is no emergency situation, an impairment analysis based on the acquired data can be performed by the control system (606). If there is no impairment, manual driving mode is activated (607). If there is an impairment, robotic driving mode is selected by activating a robotic driving device (609).

If an emergency situation is detected, emergency response protocols are initiated (608). Emergency response protocols can include activating a robotic driving device to initiate robotic driving mode (609) to re-route the vehicle to the nearest appropriate emergency response location. Emergency response protocols can also include activating the robotic driving device to control the vehicle; alerting the appropriate personnel; turning off the vehicle after arriving at the emergency response location; etc. According to further embodiments, the emergency and impairment determinations are continually processed. Thus, even if an earlier determination of no impairment or emergency was determined, a subsequent impairment or emergency situation can still be detected with the appropriate response performed by the control system (e.g., activating robotic driving or re-routing the vehicle due to a determined emergency).

According to an alternative embodiment, to avoid the possibilities of "false positives," some or all emergency situation determinations can be relayed to a remote monitoring system wherein an operator can call the vehicle to talk to an individual in the vehicle to see if an emergency actually exists. According to another embodiment, the control system can be configured to determine if an impairment or emergency exists for anyone in the vehicle in addition to the operator. Thus, various vehicle sensors can detect data regarding any or all of the vehicle's occupants.

Figure 7:
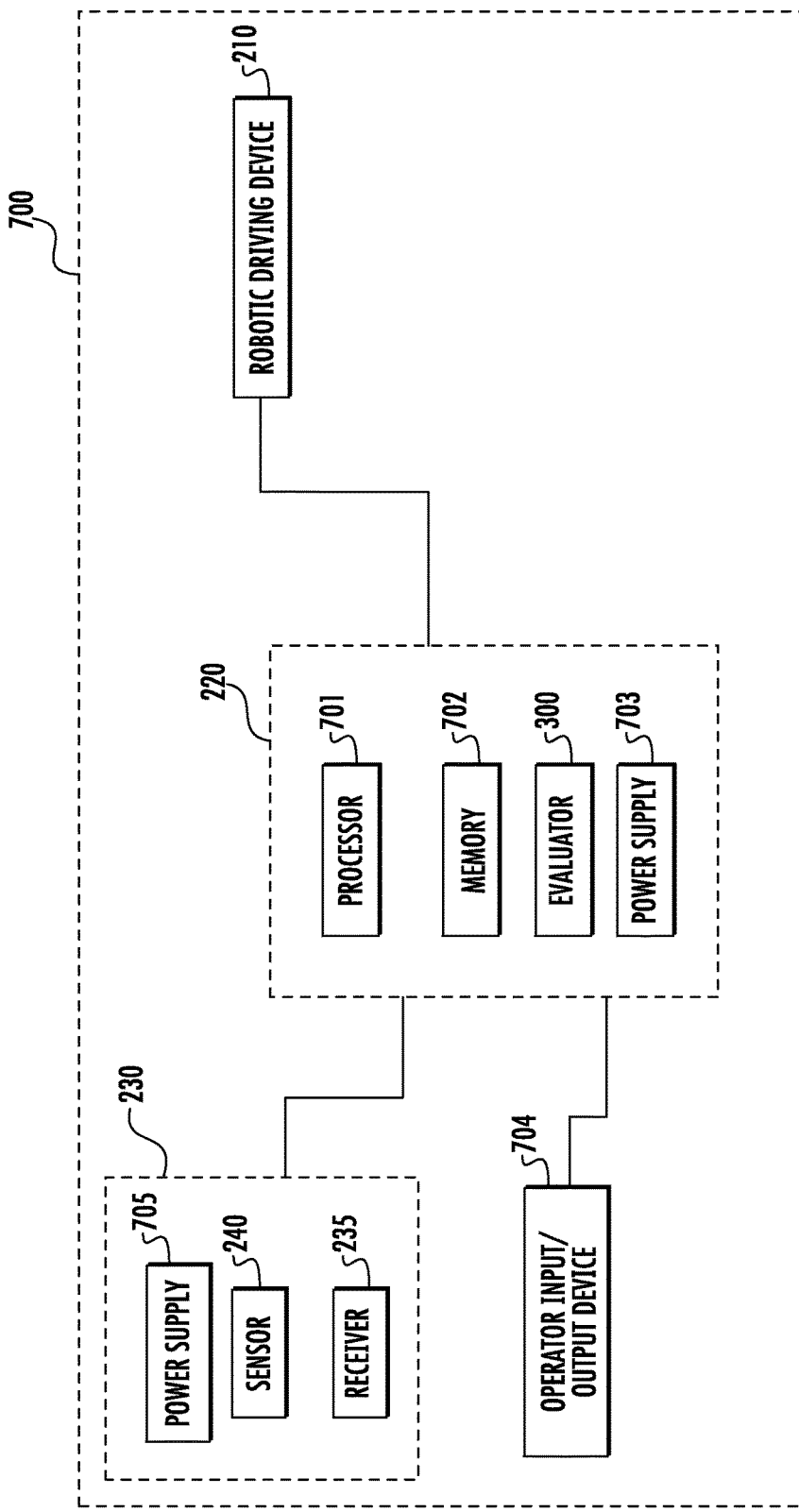
FIG. 7 is a diagram of a control system coupled to a detection system, according to one embodiment.

Referring next to FIG. 7, impaired driving avoidance system 700 is shown according to one embodiment. System 700 includes control system 220 coupled to detection system 230. System 700 also includes robotic driving device 210 and operator input/output device 704. System 700 is configured to be used in connection with many different types of vehicles including, cars, trucks, semi-trucks, buses, motorcycles, three-wheel motorcycles, trains, boats, etc. System 700 is configured to prevent a vehicle from being operated by an impaired driver.

According to one embodiment, control system 220 includes processor 701, memory 702, power supply 703, and evaluator 300. Processor 701 may be implemented as a general-purpose processor, an application specific integrated circuit (ASIC), one or more field programmable gate arrays (FGPAs), a digital-signal-processor (DSP), a group of processing components, or other suitable electronic processing components. Memory 702 is one or more devices (e.g., RAM, ROM, Flash Memory, hard disk storage, etc.) for storing data and/or computer code for facilitating the various processes described herein. Memory 702 may be or include non-transient volatile memory or non-volatile memory. Memory 702 may include database components, object code components, script components, or any other type of information structure for supporting the various activities and information structures described herein. Memory 702 may be communicably connected to processor 701 and provide computer code instructions to processor 701 for executing the processes described herein.

Detection system 230 includes sensor 240, receiver 235, and power supply 705. Control system 220 is configured to control the operation of detection system 230. Control system 220 is further configured to control operation of robotic driving device 210 and allow for operator, driver, and/or user programming through operator input/output device 704. Operator input/output device 704 is configured to enable an operator to program what data constitutes an impairment and/or an emergency in control system 220; to display acquired data to an operator; and/or to transmit commands from the operator to control system 220.

Control system 220 can communicate with detection system 230, operator input/output device 704, and robotic driving device 210 using wireless and/or wired protocols. Wireless protocols can include Wi-Fi, wireless local area network ("WLAN"), Bluetooth, radio frequency ("RF"), optical communication, infrared, microwave, sonic and ultrasonic waves, and electromagnetic induction communications platforms. Wired protocols can include fiber-optics, universal serial bus ("USB"; including all micro, mini, and standard types), twisted-pair cables, and coaxial cables.

Processor 701 is configured to analyze acquired data for operator impairment and/or potential impairment. Processor 701 is further configured to initiate robotic driving device 210 if an impairment or potential impairment is identified. In addition, processor 701 is configured to turn robotic driving device 210 off if an operator is no longer impaired. Robotic driving device 210 can have the same function and characteristics as described above. Processor 701 is further configured to transmit commands received from operator input/output device 704. For example, sensor 240 may be directed to acquire only certain types of data because an operator only chose those types of data through operator input/output device 704.

Memory 702 is configured to store pre-approved/pre-selected threshold data levels received via operator input/output device 704. Pre-approved threshold data levels correspond to driving and state characteristics of an operator as well as environmental conditions (surroundings data) internal and external to the vehicle (described in greater detail above). Processor 701 is configured to use pre-approved threshold data levels to determine whether or not an operator is impaired. In another embodiment, memory 702 is configured to store the data acquired for each operator (e.g., state and driving characteristics described above), such that processor 701 determines the presence of impairments based on comparisons with the data levels (e.g., average data levels) for each operator. Processor 701 can be pre-programmed for how much deviation from average is allowed prior to a determination of impaired being made. In a further embodiment, a combination of average data levels and pre-approved data levels can be used by processor 701 to perform an impairment analysis.

Control system 220 can be powered by power supply 703. Power supply 703 may receive power from any suitable source (e.g., rechargeable battery, non-rechargeable battery, etc.), including a vehicle's battery. Power supply 703 may also receive power through wireless inductive power, by converting mechanical energy present from operation of the vehicle into electrical energy, from solar cells, and/or through photovoltaic cells. Power supply 703 is configured to power control system 220 and detection system 230. In an alternate embodiment, power supply 705 is configured to power detection system 230. Power supply 705 can have the same characteristics to that of power supply 703 mentioned above.

As discussed in greater detail above, sensor 240 is configured to detect and acquire data regarding the operator and the surroundings, such as an operator's blood-alcohol level, medical diagnostics (e.g., heart rate, blood flow, and oxygen levels), vision acuity, radiation levels, etc. Sensor 240 can have the same function and structure as described above. Receiver 235 is configured to receive data from sensor 240. The acquired data is configured to be transmitted to control system 220 for processing.

In some embodiments, control system 220 further includes evaluator 300. Evaluator 300 is configured to receive driving commands from the operator and can have the same function and structure as described above. Evaluator 300 analyzes the commands for an impairment. Commands can include verbal and physical commands like those described above. Evaluator 300 may also include a timer programmed to intermittently start an evaluation period and configured to determine the length of the evaluation period. As such, an operator can be analyzed for impairments multiple times throughout operation of the vehicle. Moreover, evaluator 300 can be configured to allow the operator to have control of the vehicle during the evaluation period or to keep the vehicle in robotic driving mode while receiving the commands. Evaluator 300 can include or be embodied in processor 701 and/or memory 702 components. According to another configuration, evaluator 300 functions can be integrated into processor 701 and/or memory 702 of control system 220.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of analyzing an operator of a vehicle for impairment, comprising:
   acquiring data regarding an operator during operation of the vehicle;
   activating a robotic driving mode during the operation of the vehicle;
   receiving a driving command from the operator during the robotic driving mode of operation of the vehicle;
   evaluating whether the operator is impaired during the robotic driving mode of operation of the vehicle based on at least one of the data and the received driving command; and
   selectively deactivating robotic driving mode based on the evaluation.

2. The method of claim 1, further comprising deactivating robotic driving mode based on the evaluation that the operator is not impaired.

3. The method of claim 1, wherein the evaluation includes comparing effects of the operator driving commands to effects of driving commands received from a robotic driving device configured to control robotic driving mode.

4. The method of claim 3, further comprising maintaining activation of the robotic driving mode when the difference between the effects exceeds a threshold.

5. The method of claim 3, wherein robotic driving mode is deactivated when the difference between the effects is less than a threshold.

6. The method of claim 1, wherein robotic driving mode is configured to provide robotic operation of the vehicle.

7. The method of claim 1, wherein an evaluator is configured to evaluate the operator of the vehicle during an evaluation period to determine whether the operator is impaired.

8. The method of claim 7, wherein the evaluator includes a timer, wherein the timer is configured to set a length of time for an evaluation period.

9. The method of claim 8, wherein the timer is configured to set a length of time between evaluation periods.

10. The method of claim 1, wherein the driving command includes a verbal instruction.

11. The method of claim 1, wherein the driving command includes a physical command, wherein the physical command includes at least one indication of: a movement of a steering wheel of the vehicle, an application of an accelerator pedal of the vehicle, an application of a clutch pedal of the vehicle, and an application of a brake pedal of the vehicle.

12. The method of claim 1, wherein an evaluator is configured to analyze the driving commands for operator impairment.

13. The method of claim 1, further comprising repeatedly evaluating the operator while the operator is in control of the vehicle.

14. An impaired driving avoidance system, comprising:
a detection system configured to acquire data regarding an operator of a vehicle; and
a control system coupled to the detection system including an evaluator, wherein the control system is configured to:
determine that a robotic driving device is activated, such that the vehicle is in a robotic driving mode of operation;
determine whether the operator is impaired based on the data;
receive a request to deactivate the robotic driving device; and
selectively deactivate the robotic driving device based on the determination of whether an impairment exists;
wherein the evaluator is configured to constrain control of the vehicle and provide an operator with an evaluation period within which to show that the operator is not impaired.

15. The system of claim 14, wherein the control system is configured to activate the robotic driving device based on a determination that the operator is impaired.

16. The system of claim 14, wherein the control system is configured to activate the robotic driving device based on a determination of an impairment of the operator.

17. The system of claim 14, wherein the robotic driving device is configured to drive the vehicle.

18. The system of claim 14, wherein the control system includes a memory configured to store data levels for a plurality of vehicle operators.

19. The system of claim 14, further including an operator input/output device, the operator input/output device configured to display acquired data to an operator.

20. The system of claim 19, wherein the operator input/output device is configured transmit operator commands to the control system.

21. The system of claim 19, wherein the operator input/output device is configured to allow a user to program data levels that correspond to an operator impairment.

22. The system of claim 19, wherein the operator input/output device is configured to allow a user to program data levels that correspond to an emergency situation.

* * * * *